(12) United States Patent
Ludwig et al.

(10) Patent No.: US 8,187,513 B2
(45) Date of Patent: May 29, 2012

(54) METHOD FOR PRODUCING ARTICLES CONSISTING OF POLYMER MATERIALS HAVING A MEDICAMENTOUS DEPOT EFFECT

(75) Inventors: Hans-Josef Ludwig, Gelnhausen-Meerholz (DE); Bernd Hemmer, Vallendar (DE); Wilfried Mertens, Gleichamberg (DE)

(73) Assignee: Veritas AG, Gelnhausen (DE)

( * ) Notice: Subject to any disclaimer, the term of this patent is extended or adjusted under 35 U.S.C. 154(b) by 2756 days.

(21) Appl. No.: 10/483,831

(22) PCT Filed: Jul. 17, 2002

(86) PCT No.: PCT/EP02/07938
§ 371 (c)(1),
(2), (4) Date: Jul. 26, 2004

(87) PCT Pub. No.: WO03/007911
PCT Pub. Date: Jan. 30, 2003

(65) Prior Publication Data
US 2004/0251580 A1   Dec. 16, 2004

(30) Foreign Application Priority Data
Jul. 19, 2001 (DE) .................. 101 35 144

(51) Int. Cl.
*B29C 53/00* (2006.01)
(52) U.S. Cl. ........ 264/150; 264/154; 264/155; 264/156; 264/177.14; 264/209.6
(58) Field of Classification Search .................. 264/150, 264/154, 155, 156, 177.14, 209.6
See application file for complete search history.

(56) References Cited

U.S. PATENT DOCUMENTS

| 4,212,304 A | * | 7/1980 | Finney ................. 604/170.01 |
| 5,837,313 A | | 11/1998 | Ding et al. |
| 6,012,268 A | * | 1/2000 | Schunk et al. ................. 53/428 |

FOREIGN PATENT DOCUMENTS

| DE | 275 697 A | 1/1990 |
| DE | 195 17 167 A1 | 11/1996 |
| DE | 37 44 289 A | 7/1998 |
| JP | 2174703 | 7/1990 |
| WO | WO 96/35459 | 11/1996 |
| WO | WO 98 35631 A | 8/1998 |
| WO | WO 01 30407 A | 5/2001 |

OTHER PUBLICATIONS

Translation of DD 275697 to Giessmann et al (1990), 9 pages.*
Ma, et al. "Radiation crosslinked poly (vinyl methyl siloxane) for levonorgestrel delivery system"; J. Polymer Sci.; 195-9 (1988); CA Abstr. AN: 108:192710.
CA Abstr. AN: 106:68342, 1984.
CA Abstr. AN: 106:68343, 1986.

* cited by examiner

*Primary Examiner* — Christina Johnson
(74) *Attorney, Agent, or Firm* — Jacobson Holman PLLC

(57) ABSTRACT

The process for the preparation of articles from polymer materials having a medicamentous depot effect is performed by mixing the starting materials, shaping the mixture, cross-linking the polymer material at least until a sufficient dimensional stability is reached, performing all the necessary processing work, introducing the article into a protective package, sterilizing the packaged article, optionally with further cross-linking of the polymer material.

13 Claims, No Drawings

METHOD FOR PRODUCING ARTICLES CONSISTING OF POLYMER MATERIALS HAVING A MEDICAMENTOUS DEPOT EFFECT

This is a nationalization of PCT/EP02/07938 filed Jul. 17, 2002 and published in German.

The present invention relates to a process for the preparation of articles from polymer materials having a medicamentous depot effect by mixing the starting materials, shaping the mixture and cross-linking the polymer material.

From EP-B-0 824 363, a method is known for the preparation of products from polymer materials having a medicamentous depot effect in which the starting materials are mixed, the mixture is shaped into a desired form, the thus prepared form is packaged into a protective package and cross-linked and sterilized within the protective package. In principle, this method has proven useful for parts which can be introduced into the final package as non-cross-linked extrudates and/or non-cross-linked molded parts, and already represent final products suitable for sale after the cross-linking.

However, this method is unsuitable for the preparation of articles such as drainage tubings from polymer materials having a medicamentous depot effect, because, for example, the material in the non-cross-linked state is too soft and too readily deformable for the cutting out of drainage holes as well as other processing work.

According to the invention, the object of preparing articles such as drainage tubings from polymer materials having a medicamentous depot effect is achieved by mixing the starting materials, shaping the mixture, cross-linking the polymer material at least until a sufficient dimensional stability is reached, performing all the necessary processing work, introducing the article into a protective package, sterilizing the packaged article, optionally with further cross-linking of the polymer material.

The method according to the invention is particularly suitable for the preparation of drainage tubings, wherein the mixture is shaped into a tubing, cut to length, cross-linked to the necessary stability and then processed. This may include: introducing drainage holes, rounding of edges, closing of one end, inserting of T pieces and/or further supplementary parts. This is followed by the introduction of the article into a protective package, sterilizing of the packaged article, and optionally further cross-linking of the polymer material.

However, the process according to the invention is also suitable for the preparation of extrudates, molded parts, coatings on textile fabrics, wire meshes and plastic parts. They may be one-layered and multilayered, but always require processing work which has to be performed before the introduction into a protective package.

Also in the process according to the invention, the cross-linking and sterilization is preferably effected by electron beam radiation, but this process may also be effected by means of gamma rays or a combination of the two types of radiation.

For the cross-linking and sterilization, radiation doses of from 10 to 120 kGy are generally applied, radiation doses of from 20 to 66 kGy being generally sufficient.

As a polymer material for preparing articles having a medicamentous depot effect, such as drainage tubings, silicone rubber is particularly suitable. The active ingredient is preferably bound to an inorganic or organic support substance prior to mixing with the polymer material. Molecular sieves and/or layer silicates have proven particularly useful as support substances.

According to the invention, a wide variety of substances having medicinal effects may be used as active ingredients for the preparation of articles having a medicamentous depot effect. These include, for example, antithrombotic agents, antibiotics, other substances having a bactericidal or virucidal effect, local anesthetics. In the case of drainage tubings, anticoagulant substances are used, the active substance sodium pentosane polysulfate (SP 54) having proven particularly useful.

When applied within human beings, the articles according to the invention made from polymer materials having a medicamentous depot effect preferably have a marker line which is also discernable in an X-ray image. Barium sulfate, in particular, has become established as an X-ray contrast agent; if desired, a color pigment discernible with the naked eye may be added. They thus bear an X-ray active marking.

If a further filler for the polymer material is desired, calcium carbonate and other biologically inactive substances are suitable.

For performing the process according to the invention, the polymer material is mixed together with the active ingredient which may optionally be bound to a support substance, and optionally fillers, formed into an article, such as a tubing, which is cross-linked by electron beam radiation in a non-packaged state until a sufficient dimensional stability is reached. In this state, the article can then be cut to length, drainage holes can be cut out, for example, and other processing steps may be performed. For tubings, these include mainly the rounding of the cutting edges and/or closing of the end of the tubing, and/or the application of additional parts and/or T pieces.

The article prepared in this way is then sealed into a protective package and subsequently sterilized with electron beams and/or gamma rays. This may include a further cross-linking and thus mechanical stabilization of the article.

In the following Example, a typical article according to the invention and its preparation are illustrated in more detail.

EXAMPLE

Mixtures like those described in EP 0 824 363, consisting of natural rubber, chalk and a cross-linking activator and a molecular sieve/medicament adduct, or silicone rubber, chalk and a molecular sieve/medicament adduct, were extruded into a tubing and immediately precured with 15 to 25% of the total radiation dose required. Then, the tubings could be cut to length, and drainage holes could be cut out at intervals of about 3 cm. Only then, they were sealed into a protective package consisting of a polyamide sheet as in EP 0 824 363, followed by final curing with the remaining required radiation dose and thereby also sterilizing.

The preparation of these tubings was repeated, but with additionally incorporating a marking line of barium sulfate and a color pigment. Thus, tubings were formed which had an X-ray active marking and therefore remained discernible even after being introduced into the body.

The invention claimed is:
1. A process for the preparation of an article from polymer materials having a medicamentous depot effect comprising the steps of
   mixing a starting polymer material and one or more active ingredients having medicinal effects,
   shaping the mixture,
   cross-linking the polymer material in the shaped mixture at least until sufficient dimensional stability for being worked on is reached to effect a partially cured, unfinished article, working the partially cured, unfinished article,
introducing the worked article into a protective package,
sterilizing the packaged article, and
cross-linking the polymer material, further, in the packaged article.

2. The process according to claim 1, characterized in that said cross-linking and sterilization is are effected by electron beam radiation.

3. The process according to claim 1, characterized in that said cross-linking and sterilization is are effected with radiation doses of from 10 to 120 kGy.

4. The process according to claim 1, characterized in that said cross-linking and sterilization is are effected with radiation doses of from 20 to 66 kGy.

5. The process according to claim 1, characterized in that the mixture is shaped into drainage tubing before cross-linking and, after cross-linking, the partially cured drainage tubing is worked by a processing comprising the steps of
cutting the tubing to length,
application of drainage holes,
rounding of cutting edges,
closing of one end of the tubing lengths, and
application of additional parts.

6. The process according to claim 1, characterized in that silicone rubber is used as the starting polymer material.

7. The process according to claim 1, characterized in that an active ingredient or ingredients are bound to an inorganic or organic support substance are mixed with the starting polymer material.

8. The process according to claim 7, characterized in that molecular sieves and/or layer silicates are used as said support substance.

9. The process according to claim 1, characterized in that the one or more active ingredients having medicinal effects have anticoagulant effects.

10. The process according to claim 1, characterized in that the article is marked with an X-ray active marking.

11. The process according to claim 10, characterized in that said X-ray active marking is a line of X-ray contrast agent containing barium sulfate and a visually discernible color.

12. The process according to claim 1, characterized in that calcium carbonate or other inactive fillers are mixed with the starting polymer material.

13. The process according to claim 1, characterized in that the sterilization is effected with beta and/or gamma radiation after the packaging.

* * * * *